United States Patent
Li et al.

(10) Patent No.: US 7,491,153 B2
(45) Date of Patent: Feb. 17, 2009

(54) COMBINED EXERCISE MANAGEMENT AND ENTERTAINMENT UNIT

(75) Inventors: Chun-Hsing Li, Chiayi (TW); Yen-Jen Chen, Taipei (TW)

(73) Assignee: Mitac Technology Corp., Hsin-Chu Hsien (TW)

( * ) Notice: Subject to any disclaimer, the term of this patent is extended or adjusted under 35 U.S.C. 154(b) by 88 days.

(21) Appl. No.: 11/598,637

(22) Filed: Nov. 14, 2006

(65) Prior Publication Data
US 2007/0243974 A1   Oct. 18, 2007

(30) Foreign Application Priority Data
Apr. 12, 2006   (TW) .............................. 95113072 A

(51) Int. Cl.
*A63B 21/00* (2006.01)
(52) U.S. Cl. .................................. 482/8; 482/1; 482/9
(58) Field of Classification Search ................. 482/1–9, 482/51, 900–902; 434/247
See application file for complete search history.

(56) References Cited

U.S. PATENT DOCUMENTS

| 5,067,710 | A  | * | 11/1991 | Watterson et al. .............. 482/3 |
| 6,852,068 | B2 | * | 2/2005  | Ogawa .......................... 482/8 |
| 7,189,191 | B2 | * | 3/2007  | Dugan ........................... 482/8 |

* cited by examiner

*Primary Examiner*—Glenn Richman
(74) *Attorney, Agent, or Firm*—Rosenberg, Klein & Lee

(57) ABSTRACT

A combined exercise management and entertainment unit includes a sensor for sensing a user's body state during exercise and producing an exercise signal to a microprocessor, so as to calculate the user's calorie consumption during exercise each time and the accumulated calorie consumption; a personal characteristics database for storing data of a user's body physical characteristics; an exercise course memory for storing exercise courses set by the user, including the time period, item, and duration of an exercise to be done; a setting unit for the user to set the data of body physical characteristics to be stored in the personal characteristics database; and a play unit having an entertainment information memory for storing a plurality of entertainment information entries, which correspond to the exercise items set by the user and may be selectively played corresponding to the exercise item being done.

11 Claims, 8 Drawing Sheets

COMBINED EXERCISE MANAGEMENT AND ENTERTAINMENT UNIT

FIELD OF THE INVENTION

The present invention relates to an exercise management unit, and more particularly to a combined exercise management and entertainment unit.

BACKGROUND OF THE INVENTION

With the rapidly developed society and the largely upgraded living quality, people's food has been largely diversified. Generally, most people in the modern society have too much or inadequate diet, busy works, and insufficient exercise to result in degraded body functions, fatness, and illness.

However, in recent years, people start paying attention to their health condition and the benefit of doing exercise, and various kinds of exercise equipment and instruments good for the health have been developed and introduced into market. Since most people doing exercise want to accurately control the amount and intensity of exercise, and to clearly know their body physical state during exercise, many exercise management devices have been developed to meet this demand. These exercise management devices include many detecting devices designed to reflect the user's body state during exercise, such as heartbeat/pulse sensor, blood pressure monitor, body mass index (BMI) measuring meter, pedometer, etc.

On the other hand, there are also many people pay a lot of attention to their entertainments after work. Various kinds of entertainment products have also been developed. Entertainment products that can be conveniently carried along with the user, such as walkman, portable music player, etc., are particularly welcome among consumers.

However, in the currently commercially available products, the music players and the exercise and body signal detecting devices are independently produced. That is, there is not any product that combines an exercise management device and a music player.

While there are various kinds of exercise management devices available in the market, these devices are simply designed to detect the user's body condition during exercise. And, while these exercise management devices may accurately measure the user's body state during exercise, they do not interact with the user or provide any good recommendation when the user finishes doing exercise.

SUMMARY OF THE INVENTION

A primary object of the present invention is to provide a combined exercise management and entertainment unit, which allows a user to select a digital musical data for listening during exercise while the selected musical data has a specific rhythm corresponding to the intensity of an exercise item being done.

Another object of the present invention is to provide an exercise management unit capable of showing adequate exercise recommendations according to a user's health condition when the exercise is finished.

A further object of the present invention is to provide an exercise management unit adapted to emit a sound reminder or warning when a user's heartbeat during exercise has reached a preset frequency or exceeded a preset load.

A still further object of the present invention is to provide an exercise management unit adapted to provide recipes, so that a user may check and calculate calorie contents of different foods, as well as receive many different diet menus.

A still further object of the present invention is to provide an exercise management unit that may be linked with a second exercise management unit at a remote location by connecting the first unit to a computer apparatus via a data transmission interface, and connecting the computer apparatus to the second unit via the Internet, such that two users of the present invention may contest with each other during exercise.

To achieve the above-mentioned objectives, in accordance with the present invention, a combined exercise management and entertainment unit includes a sensor for sensing a user's body state during exercise and producing an exercise signal to a microprocessor, so as to calculate the user's calorie consumption during exercise each time and the accumulated calorie consumption; a personal characteristics database for storing data of a user's body physical characteristics; an exercise course memory for storing exercise courses set by the user, including the time period, item, and duration of an exercise to be done; a setting unit for the user to set the data of body physical characteristics to be stored in the personal characteristics database; and a play unit having an entertainment information memory for storing a plurality of entertainment information entries, which correspond to the exercise items set by the user and may be selectively played corresponding to the exercise item being done.

Unlike the prior art, the present invention combines a play unit with an exercise management unit, and digital musical data of different rhythms may be selectively played corresponding to a user-selected exercise item of a specific intensity, so that the user may entertain himself or herself while doing exercise. The present invention also allows the user to set exercise courses meeting personal body requirements, so as to help the user to do exercise regularly and know his or her exact health condition, such as heartbeat rate, body fat distribution, etc.

When the user finishes doing exercise, the present invention also provides the user with suitable exercise recommendations according to the user's body condition. The present invention also plan for the user effective solutions of weight loss, dietary intake control, including the provision of information about calorie consumption, calorie contents of different foods, calculation of personal required calories, etc., and diet menus, so as to improve the user's body functions and help the user to maintain good health condition.

The combined exercise management and entertainment unit of the present invention may be linked with a computer apparatus via a data transmission interface, so as to transmit or receive different entertainment information. The present invention also allows the user to store personal exercise data in a computer and to track these data via a network. The user of the present invention may contest with a remote user during exercise through linking the two exercise management units via the Internet. In the present invention, game software may be utilized in the exercise course, so as to attract and encourage the user to keep doing exercise regularly through good interaction with the unit. In brief, the unit of the present invention not only enables users to entertain themselves and interact with the unit, but also helps the users to effectively obtain the effect of weight loss, and is therefore a commercially very practical product with excellent added value.

BRIEF DESCRIPTION OF THE DRAWINGS

The structure and the technical means adopted by the present invention to achieve the above and other objects can be best understood by referring to the following detailed description of the preferred embodiments and the accompanying drawings, wherein FIG. 1 schematically shows a combined exercise management and entertainment unit according to the present invention is worn on a user's body during exercise.

DETAILED DESCRIPTION OF THE PREFERRED EMBODIMENTS

Figure 1:
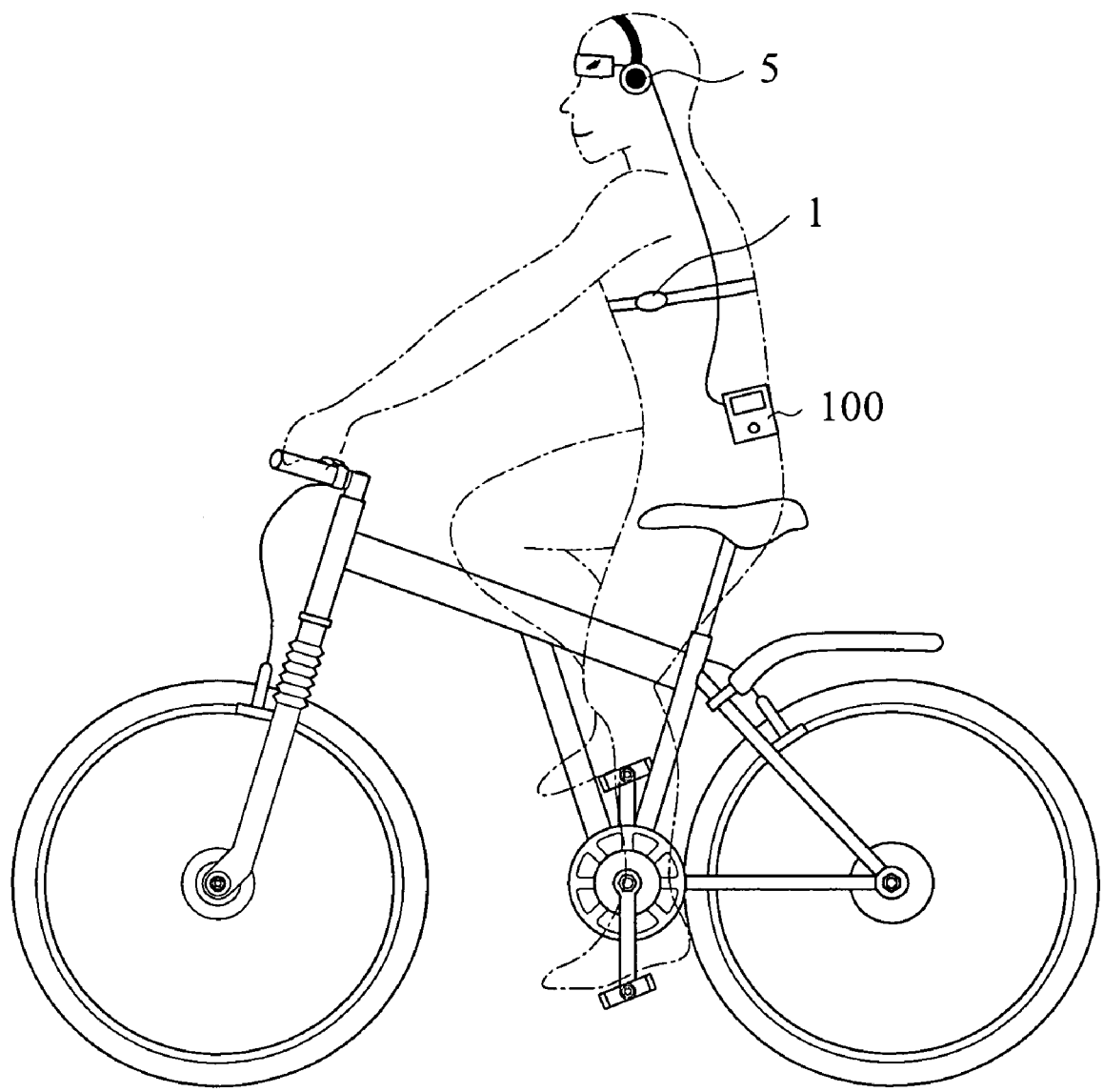

Please refer to FIG. 1. A combined exercise management and entertainment unit 100 according to the present invention is designed for wearing on a user's body at any suitable area. For the purpose of conciseness, the present invention is also briefly referred to as "the unit 100" herein. As shown, the unit 100 includes an exercise signal sensor 1 for sensing the user's body state during exercise. In the illustrated embodiment, the exercise signal sensor 1 is a heartbeat detector for sensing the user's heartbeat during exercise.

Figure 2:
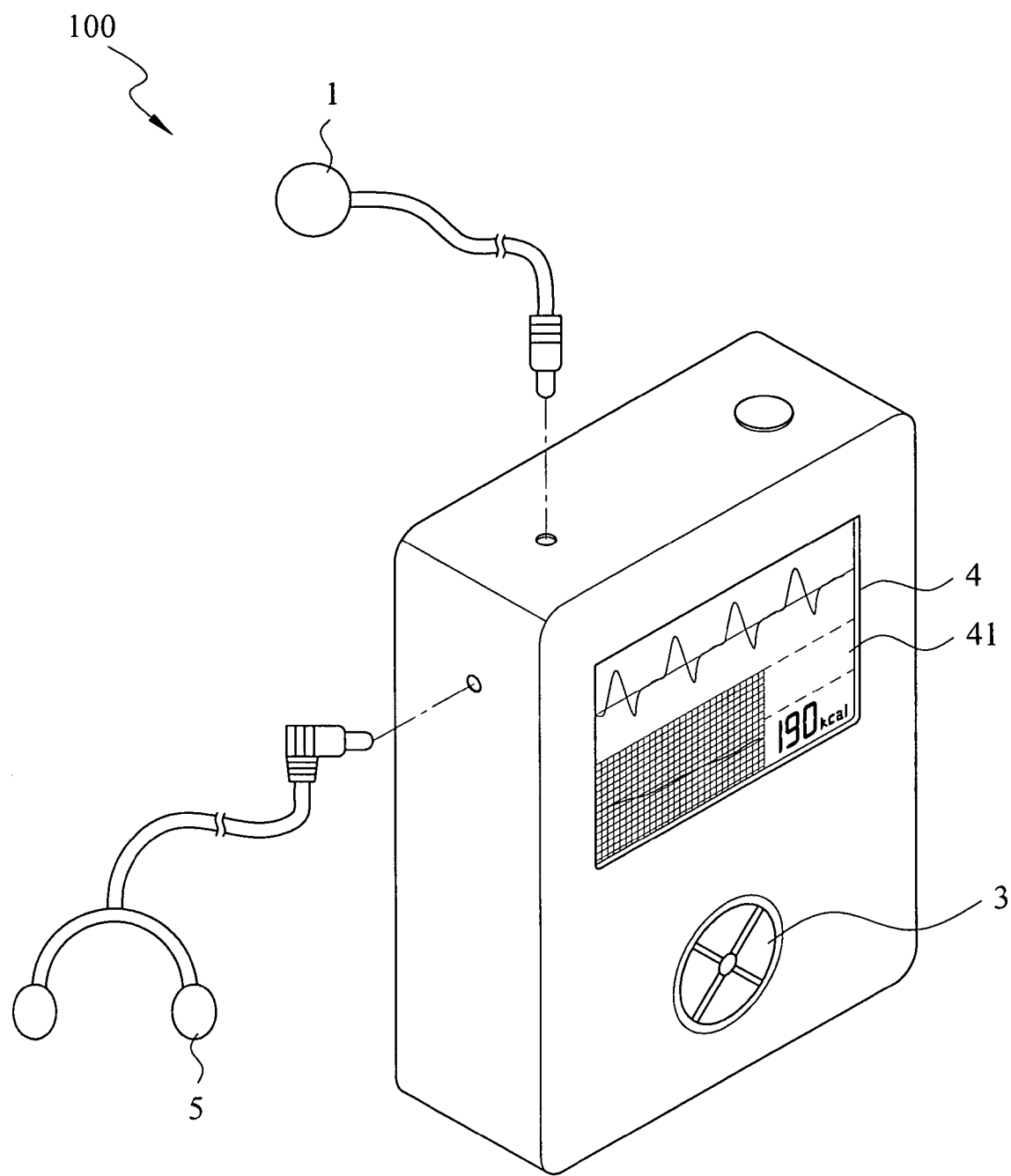
FIG. 2 is a perspective view of the combined exercise management and entertainment unit of the present invention.
Figure 3:
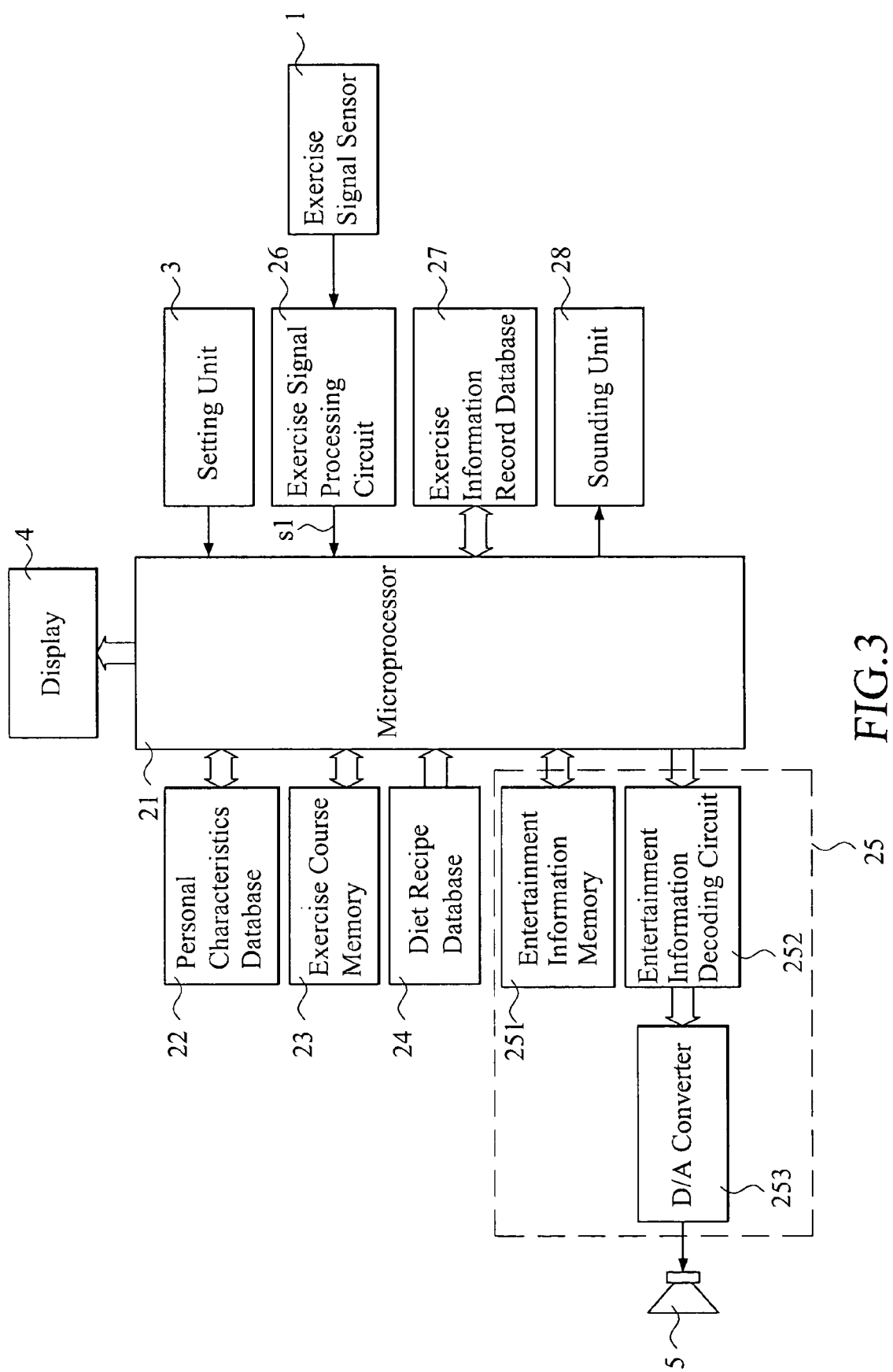
FIG. 3 is a block diagram of a first embodiment of the present invention.

Please refer to FIG. 2 that is a perspective view showing an appearance of the unit 100 of the present invention, and to FIG. 3 that is a block diagram of the unit 100 according to a first embodiment of the present invention. As shown, the unit 100 of the present invention combines entertainment and exercise management functions, so that a user may enjoy music, games, or the like during exercise to get more fun. The entertainment function may include the play of musical information and/or the play of audio/video (A/V) information. In the following embodiments described with reference to the accompanied drawings, the entertainment function of the present invention means the play of digital musical data (i.e., MP3).

As shown in FIG. 3, the unit 100 includes a microprocessor 21 electrically connected to a personal characteristics database 22, an exercise course memory 23, a diet recipe database 24, a play unit 25, a setting unit 3, and a display 4.

The personal characteristics database 22 stores data of the user's body physical characteristics. The exercise course memory 23 stores different exercise courses set by the user, and each of the exercise courses includes data about the time period, the item, and the duration of each exercise to be done, and the projected Calorie (Cal) consumption. The diet recipe database 24 stores information on the calorie contents of different foods and diet menus.

The play unit 25 includes an entertainment information memory 251, an entertainment information decoding circuit 252, and a digital to analog converter 253 (D/A converter). The entertainment information memory 251 stores a plurality of entries of entertainment information, which separately correspond to a different exercise item stored in the exercise course memory 23. When the user is doing one exercise item, one of the entertainment information entries corresponding to that exercise item is decoded by the entertainment information decoding circuit 252 and converted by the digital to analog converter 253, so as to be played via a play device 5.

The unit 100 further includes an exercise signal processing circuit 26, which is also electrically connected to the microprocessor 21. When the exercise signal sensor 1 senses the user's heartbeats during exercise, information about the detected heartbeats is processed by the exercise signal processing circuit 26 to produce an exercise signal s1, which is then sent to the microprocessor 21. The exercise signal processing circuit 26 may includes an amplifier, a filter circuit, and a signal shaping circuit that are known to the art.

The microprocessor 21 calculates the calorie consumption in each exercise item each time and the accumulated calorie consumption, based on the exercise signal s1, the data of body physical characteristics stored in the personal characteristics database 22, and the exercise item in the exercise course being executed. The calculated information on the calorie consumption is then stored in an exercise information record database 27 electrically connected to the microprocessor 21. The exercise information record database 27 stores information about the exerciser's heartbeat count during exercise each time, the highest record of the exerciser's heartbeat count, the calorie consumption during exercise each time, and the accumulated calorie consumption up to date.

The setting unit 3 allows a user to set data of personal body physical characteristics for storing in the personal characteristics database 22, the exercise courses for storing in the exercise course memory 23, and musical data corresponding to the exercise items set in the exercise course memory 23.

The display 4 displays different exercise information and the user's body state during exercise, including the exercise signal s1, personal body physical characteristics, exercise courses, exercise item being done, and calorie consumption during exercise as calculated by the microprocessor 21. The display 4 further includes a zone 41 particularly for displaying exercise recommendations, which are made based on the calorie consumption during exercise calculated by the microprocessor 21 and provided as a reference for the user.

The microprocessor 21 of the unit 100 further includes a sounding unit 28. When the exercise signal sensor 1 detects the user's heartbeat count during exercise, a sound is emitted by the sounding unit 28 to remind or warn the user that his or her heartbeat count has reached, exceeded, or not reached a desired value. Meanwhile, a proper exercise course previously set by the user is timely recommended to the user.

Figure 4:
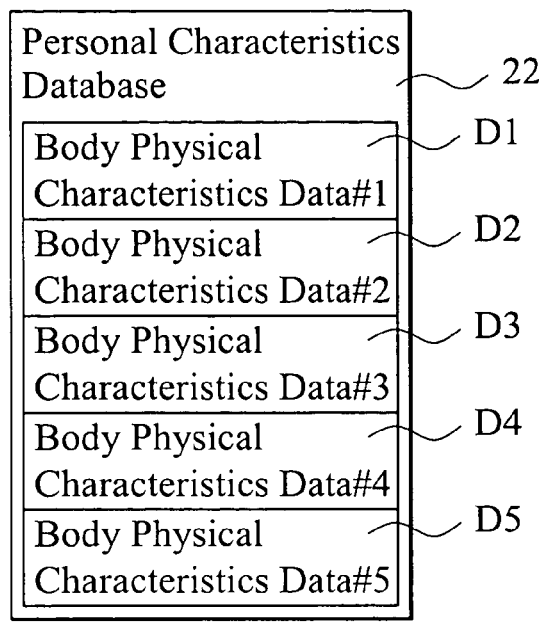
FIG. 4 is a conceptual view showing data of user's body physical characteristics stored in a personal characteristics database built in the present invention.

Please refer to FIG. 4. The personal characteristics database 22 may store a large quantity of data D1, D2, D3, D4, and D5 of the user's body physical characteristics. The body physical characteristics data D1 through D5 may include, for example, the user's height, weight, daily calorie consumption, body fat, body mass index (BMI), etc. The contents of the body physical characteristics data D1 to D5, such as the user's age, sex, blood pressure, blood glucose, body fat distribution, etc., may be varied according to an actual application of the unit 100.

Figure 5:
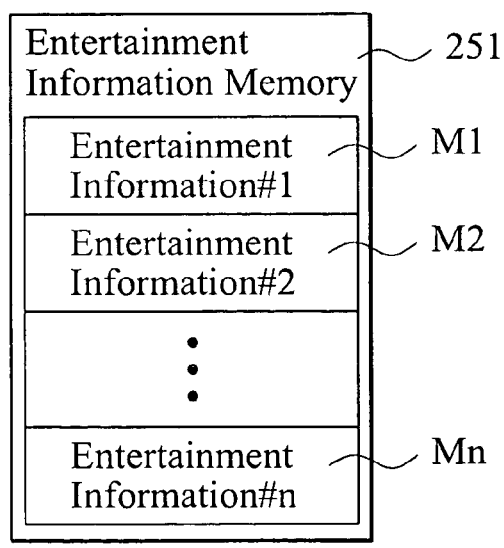
FIG. 5 is a conceptual view showing musical data stored in a musical memory built in the present invention.

FIG. 5 shows the entertainment information memory 251 may store multiple entries of entertainment information M1, M2 . . . , and Mn, which separately correspond to a different exercise item stored in the exercise course memory 23. The entertainment information entries M1, M2, ..., and Mn are musical data, and the user may select one of the musical data having a specific rhythm corresponding to the intensity of the selected exercise item. For instance, a musical data with moderate rhythm is selected for a low-intensity exercise, and a musical data with quick rhythm is selected for a high-intensity exercise. In the illustrated embodiments of the present invention, the entertainment data entries M1, M2, ..., and Mn are general digital musical data.

Figure 6:
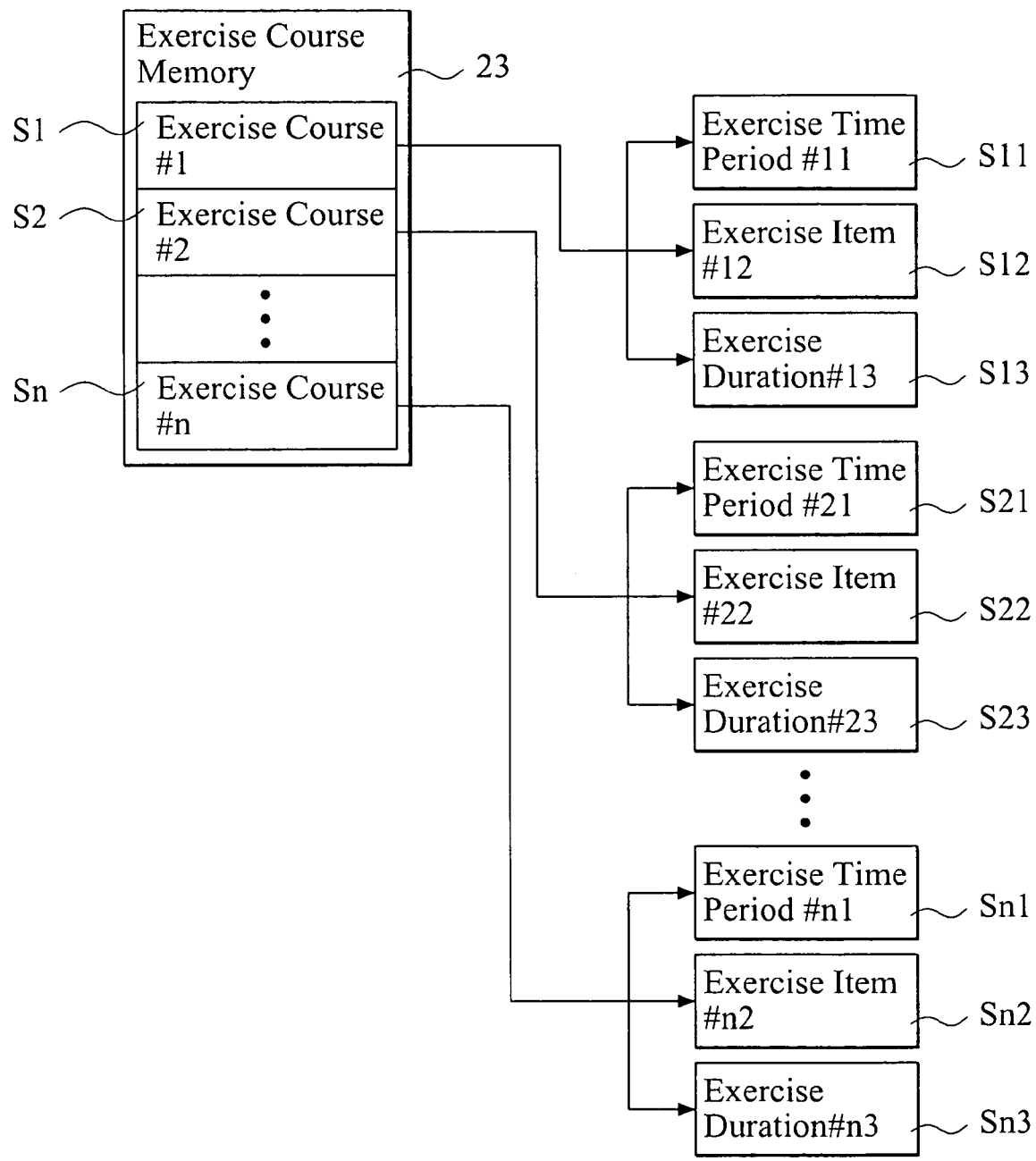
FIG. 6 is a conceptual view showing exercise courses stored in an exercise course memory built in the present invention.

FIG. 6 shows the exercise course memory 23 stores a plurality of exercise courses S1, S2, ..., and Sn that are set by the user. Each of the exercise courses S1 to Sn includes details thereof, such as the exercise time period S11, S21, ..., and Sn1 for each exercise course, the exercise items S12, S22, ..., and Sn2 included in each exercise course, and the duration S13, S23, ..., and Sn3 for each exercise item each time. Moreover, the exercise courses S1, S2, ..., and Sn separately correspond to the musical data M1, M2, ..., and Mn.

Figure 7:
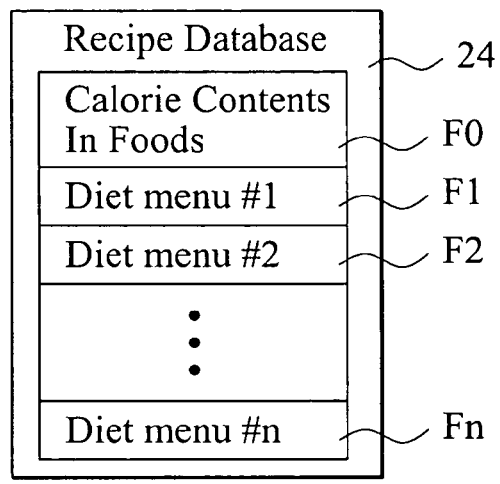
FIG. 7 is a conceptual view showing diet information stored in a recipe database built in the present invention.

FIG. 7 shows the diet recipe database 24 stores information on calorie contents of different foods F0, such as the calculation and inquiry of food calorie content, and a plurality of diet menus F1, F2, ..., and Fn, so as to provide the user with diet menus that satisfy the user's need in balanced food.

Figure 8:
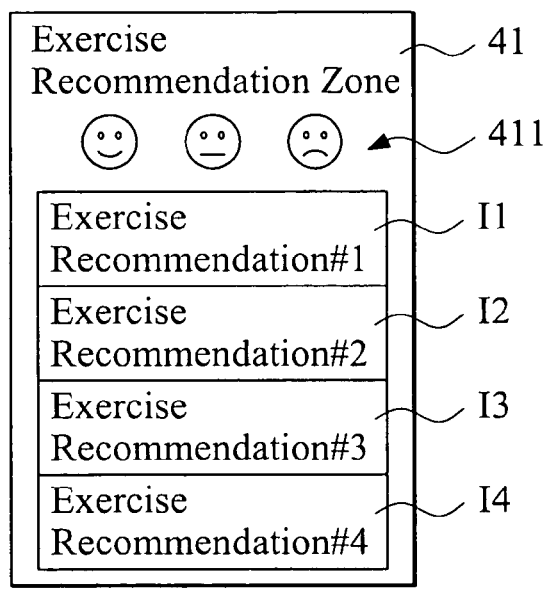
FIG. 8 is a conceptual view showing exercise recommendations shown in an Exercise Recommendation Zone on a display of the present invention.

FIG. 8 shows the exercise recommendation zone 41 on the display 4 may show different expression icons 411 and many different exercise recommendations I1, I2, I3, and I4. One of the expression icons 411 would be automatically shown when the unit 100 is turned on or when the user is in a certain body state during exercise, so that the user may clearly know from the simple and easily understood expression icons whether the currently accumulated exercise intensity and calorie consumption are in a good, normal, or insufficient condition.

The exercise recommendations I1, I2, I3, and I4 may include, for example, the required time for recovery, the dietary intake, the daily calorie consumption, and the estimated duration for weight loss. Moreover, such exercise recommendations I1, I2, I3, and I4 may also provide the user with effective weight-loss program, diet menus, and exercise time table according to the user's current health condition.

Figure 9:
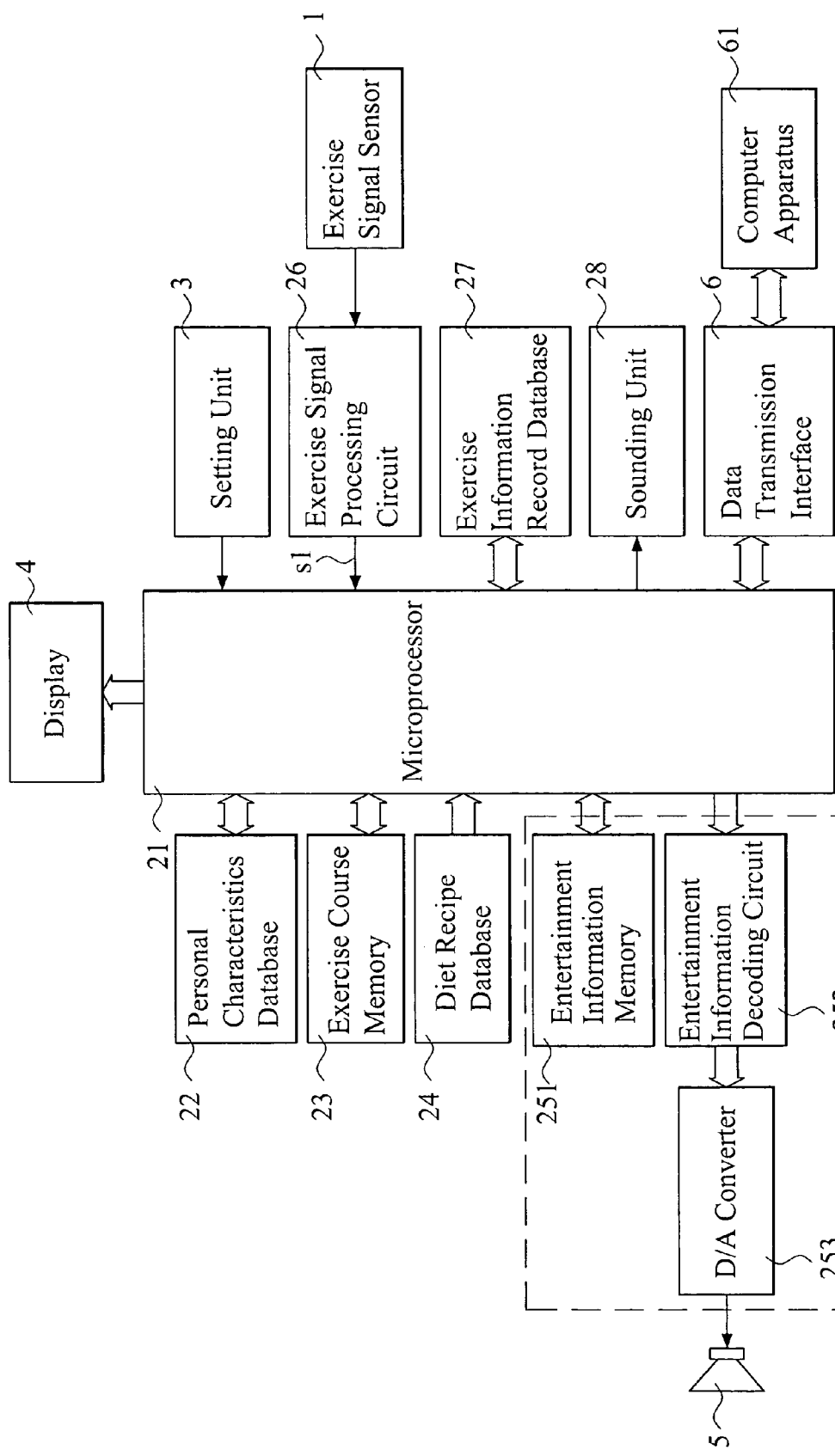
FIG. 9 is a block diagram of a combined exercise management and entertainment unit according to a second embodiment of the present invention.

Please refer to FIG. 9 that is a circuit block diagram of a combined exercise management and entertainment unit 100 according to a second embodiment of the present invention. In the second embodiment, the microprocessor 21 is electrically connected to a data transmission interface 6, which may be further connected to a computer apparatus 61, so that the unit 100 may transmit the entertainment information M1, M2, ..., and Mn to the computer apparatus 61 or receive entertainment information from the computer apparatus 61.

Figure 10:
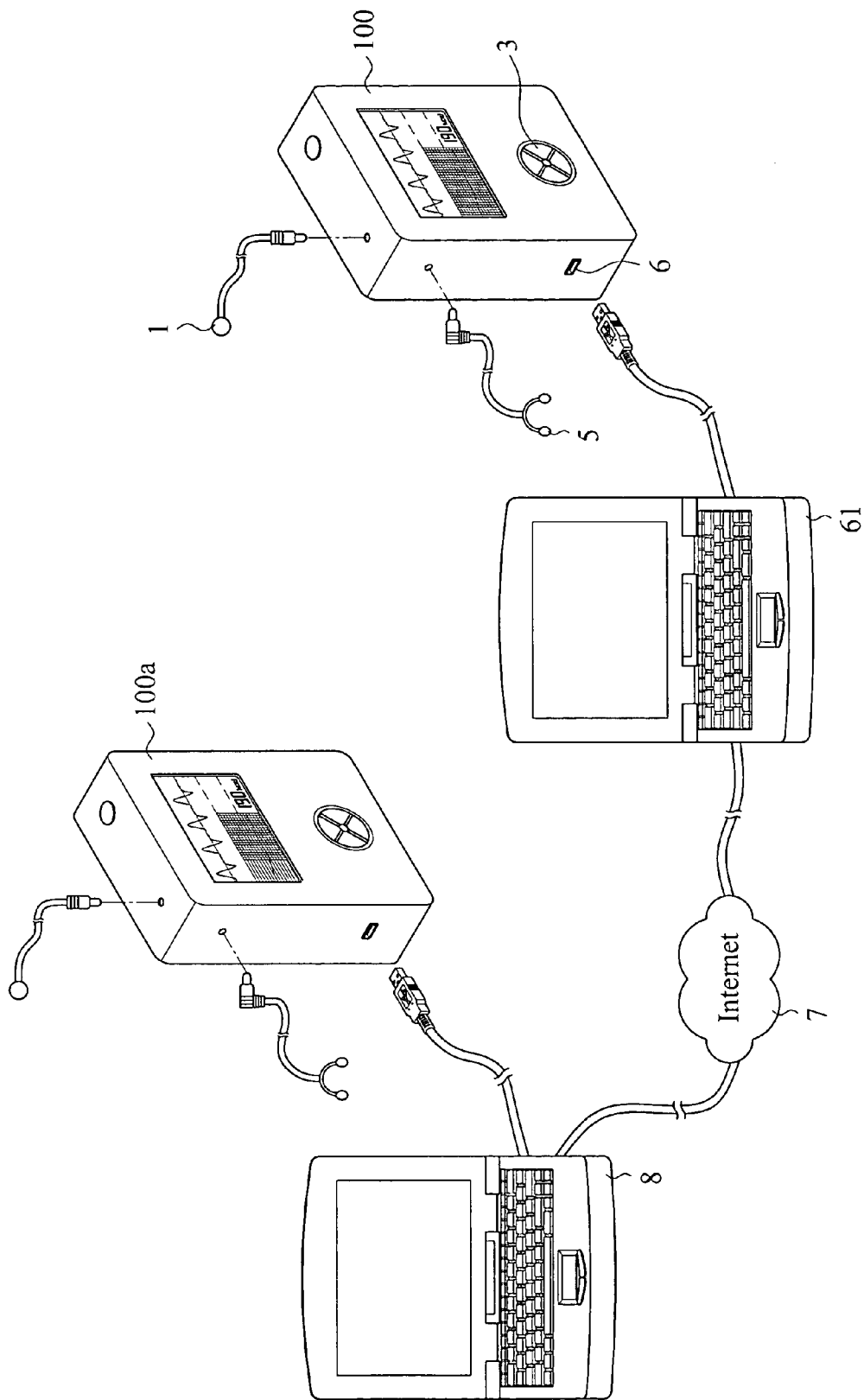
FIG. 10 is a conceptual view showing the connection of the present invention to a remote computer apparatus via the Internet.

As can be seen from FIG. 10, the computer apparatus 61 may be linked with a remote computer apparatus 8 via an Internet interface and the Internet 7, so that the user may transmit the entertainment information M1, M2, ..., and Mn from the unit 100 to the remote computer apparatus 8 via the Internet 7, or to receive entertainment information transmitted from the remote computer apparatus 8. Moreover, the user may also store data of personal body state during exercise in the computer apparatus 61 and track the data via the Internet 7.

Via the Internet 7, the user of the unit 100 may contest with another user who uses another unit 100a connected to the remote computer apparatus 8, making the exercise more interesting and allowing an interaction between two units 100 and 100a. A proper contest among different users of the combined exercise management and entertainment unit of the present invention may advantageously drive the users to do exercise constantly and actively while enjoy music at the same time.

Before doing exercise, a user may utilize the unit 100 to arrange some required exercise courses, set projected calorie consumption, and establish a time table. When the unit 100 is worn on the user's body and turned on, one of the expression icons 411 is shown in the exercise recommendation zone 41, allowing the user to clearly know from the simple and easily understood expression icon 411 whether the user's currently accumulated exercise intensity and calorie consumption are in a good, normal, or insufficient condition, and therefore accurately controls personal exercise state. Moreover, the user may select musical data of a specific rhythm corresponding to the intensity of the selected exercise item to enjoy exercise and entertainment at the same time.

As soon as the user starts doing exercise, the unit 100 senses the user's heartbeats and automatically records the calorie consumption in each exercise item each time, the accumulated calorie consumption, the heartbeat frequency, etc. The unit 100 automatically provides such data according to the user's body condition during exercise for the user's reference.

After the exercise is finished, information about the required time for recovery/rest, the suggested dietary intake, the calculated calorie consumption, etc. is automatically shown in the exercise recommendation zone 41 on the display 4 of the unit 100. A target plan of weight-loss is also designed for the user's reference. Therefore, with the combined exercise management and entertainment unit 100 of the present invention, the user may timely monitor personal health condition before, during, and after exercise, and to most effectively achieve the purpose of losing weight.

What is claimed is:

1. A combined exercise management and entertainment unit, comprising:

a sensor for sensing a user's body state during exercise, the body state during exercise being processed by an exercise signal processing circuit to produce an exercise signal;

a personal characteristics database for storing data of the user's body physical characteristics;

an exercise course memory for storing exercise courses set by the user, each of the exercise courses including information about any of exercise time period, exercise items, duration of each exercise item each time, and combination thereof;

a setting unit for the user to set the data of body physical characteristics for storing in the personal characteristics database, the exercise courses for storing in the exercise course memory, and a plurality of entertainment information entries corresponding to the individual exercise items set in the exercise course memory;

a microprocessor adapted to receive the exercise signal produced by the sensor, and calculate calorie consumption in each exercise item each time and accumulated calorie consumption based on the exercise signal received from the sensor, the data of body physical characteristics stored in the personal characteristics database, and the exercise items included in the exercise course being executed;

a display for showing any of the exercise signal, the data of personal body physical characteristics, the exercise courses, the exercise items, the calculated calorie consumption, and combination thereof; and a play unit having an entertainment information memory for storing a plurality of entries of entertainment information that separately correspond to the exercise items set in the exercise course memory, so that the user may select to play one of the entertainment information entries corresponding to an exercise item being done.

2. The combined exercise management and entertainment unit as claimed in claim 1, wherein the sensor is a heartbeat detector for sensing the user's heartbeats during exercise.

3. The combined exercise management and entertainment unit as claimed in claim 1, wherein the data of body physical characteristics stored in the personal characteristics database includes the user's height, weight, required daily calorie consumption, body fat, and body mass index.

4. The combined exercise management and entertainment unit as claimed in claim 1, wherein the entertainment information entries corresponding to the exercise items set in the exercise course memory are musical data, and the musical data having different rhythms and being selected according to an intensity of the exercise item being done.

5. The combined exercise management and entertainment unit as claimed in claim 1, wherein the entertainment information stored in the entertainment information memory are digital musical data.

6. The combined exercise management and entertainment unit as claimed in claim 1, further comprising a recipe database for storing information about calorie contents of different foods and diet menus.

7. The combined exercise management and entertainment unit as claimed in claim 1, wherein the display is provided with an exercise recommendation zone for showing exercise recommendations, the exercise recommendations being provided by the microprocessor based on the exercise signal, the data of body physical characteristics stored in the personal characteristics database, the calorie consumption calculated according to the exercise items in the exercise course being executed; and the exercise recommendations including information about time required for recovery, dietary intake, daily calorie consumption, and estimated weight-loss duration for the user.

8. The combined exercise management and entertainment unit as claimed in claim 1, further comprising a sounding unit, whereby when the sensor detects the user's heartbeats during exercise, a sound is emitted by the sounding unit to remind or warn the user that his or her heartbeat count has reached, exceeded, or not reached a desired value.

9. The combined exercise management and entertainment unit as claimed in claim 1, further comprising a data transmission interface adapted to connect to a computer apparatus, such that the entertainment information may be transmitted to or received from the computer apparatus.

10. The combined exercise management and entertainment unit as claimed in claim 9, wherein the computer apparatus is adapted to link with a remote computer apparatus via an Internet interface and the Internet, so that the entertainment information may be transmitted to or received from the remote computer apparatus via the Internet.

11. The combined exercise management and entertainment unit as claimed in claim 1, wherein the entertainment information entries corresponding to the exercise items set in the exercise course memory are musical data, and the musical data having a specific rhythm corresponding to the intensity of the exercise process being performed by the user, the specific rhythm of the musical data is dependent and directly correlated to the intensity of the exercise process.

* * * * *